United States Patent [19]

Mertens et al.

[11] Patent Number: 4,824,835
[45] Date of Patent: Apr. 25, 1989

[54] ISOQUINOLINEDIONE DERIVATIVES, PHARMACEUTICAL COMPOSITIONS AND METHODS OF USE

[75] Inventors: Alfred Mertens, Schriesheim; Bernd Müller-Beckmann, Grünstadt, both of Fed. Rep. of Germany

[73] Assignee: Boehringer Mannheim GmbH, Mannheim, Fed. Rep. of Germany

[21] Appl. No.: 42,300

[22] Filed: Apr. 24, 1987

[30] Foreign Application Priority Data

Apr. 25, 1986 [DE] Fed. Rep. of Germany ....... 3614000

[51] Int. Cl.$^4$ .................... A61K 31/47; C07D 217/24; C07D 401/12
[52] U.S. Cl. .................... 514/278; 514/309; 546/18; 546/142
[58] Field of Search .................. 514/278, 309; 546/18, 546/142

[56] References Cited

U.S. PATENT DOCUMENTS 3,406,175 10/1968 Lesher .................................. 546/16
4,021,558 5/1977 Kutter et al. ......................... 546/142

Primary Examiner—Robert T. Bond
Attorney, Agent, or Firm—Felfe & Lynch

[57] ABSTRACT

The present invention provides isoquinolinedione derivatives of the general formula:

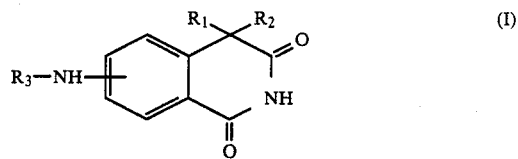

wherein $R_1$ is a hydrogen atom or an alkyl, alkenyl or cycloalkyl radical which is optionally interrupted by a heteroatom or by a heteroatom substituted with an alkyl radical, $R_2$ is a hydrogen atom or an alkyl or alkenyl radical, or together with $R_1$, represents a cycloalkylene, alkylidene or cycloalkylidene radical which is optionally interrupted by a heteroatom or by a heteroatom substituted by an alkyl radical and $R_3$ is a radical of the general formula:

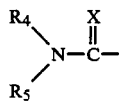

which can be in the 5- 6-, 7- or 8-position of the isoquinoline-1,3-dione and in which $R_4$ and $R_5$, which can be the same or different, are hydrogen atoms or alkyl, trihaloalkyl, cycloalkyl, cycloalkenyl, dealkylaminoalkyl, alkoxycarbonylalkyl, alkylcarbonyl, aryl or heterayl radicals and X is an oxygen or sulphur atom or a radical of the general formula $=N-R_6$, in which $R_6$ is a hydrogen atom, a cyano group of an alkyl radical; and the physiologically acceptable salts thereof.

The present invention also provides processes for the preparation of these compounds and pharmaceutical compositions containing them. These new compounds have a blood pressure lowering effect and/or influence thrombocyte aggregation, improve the microcirculation, and exert a positive intropic effect, thus having therapeutic and prophylactic effects.

23 Claims, No Drawings

ISOQUINOLINEDIONE DERIVATIVES, PHARMACEUTICAL COMPOSITIONS AND METHODS OF USE

The present invention is concerned with new isoquinoline-1,3-diones, with processes for the preparation thereof and with pharmaceutical compositions containing them.

The new isoquinoline-1,3-diones according to the present invention are compounds of the general formula:

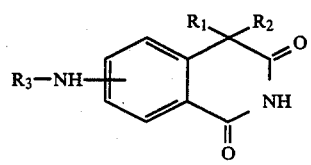

wherein $R_1$ is a hydrogen atom or an alkyl, alkenyl or cycloalkyl radical which is optionally interrupted by a heteroatom or by a heteroatom substituted with an alkyl radical, $R_2$ is a hydrogen atom, an alkyl or alkenyl radical or, together with $R_1$, forms a cycloalkylene, alkylidene or cycloalkylidene radical which is optionally interrupted by a heteroatom or by a heteroatom substituted with an alkyl radical and $R_3$ is a radical of the general formula:

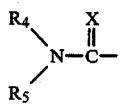

which can be in the 5-, 6-, 7- or 8-position of the isoquinoline-1,3-dione and in which $R_4$ and $R_5$, which can be the same or different, are hydrogen atoms or alkyl, trihaloalkyl, cycloalkyl, cycloalkenyl, dialkylaminoalkyl, alkoxycarbonylalkyl, alkylcarbonyl, aryl or heteroaryl radicals and X is an oxygen or sulphur atom or a radical of the general formula $=N-R_6$, in which $R_6$ is a hydrogen atom, an alkyl radical or a cyano group; and the physiologically acceptable salts thereof.

Since, when $R_1$ is not the same as $R_2$, the compounds of general formula (I) contain an asymmetric carbon atom, the present invention also includes the optically-active forms and the racemic mixtures of these compounds.

The new compounds according to the present invention possess valuable pharmacological properties and, in particular, they increase the strength of the heart and/or have a blood pressure lowering action and/or influence the thrombocyte aggregation and improve the microcirculation.

In general formula (I), the symbols $R_1$ and $R_2$ signify hydrogen atoms or straight-chained or branched alkyl or alkenyl radicals with 1 to 6 or 2 to 6 carbon atoms, respectively. In particular, they signify hydrogen atoms or methyl, ethyl or allyl radicals.

If only $R_2$ represents a hydrogen atom, then $R_1$ can also be a branched alkyl or cycloalkyl radical containing 3 to 7 carbon atoms which is optionally interrupted by a heteroatom or by a heteroatom substituted by an alkyl radical. Preferred in this sense are isopropyl, 3-pentyl, cyclopentyl, cyclohexyl, piperidyl and N-methylpiperidyl radicals.

$R_1$ and $R_2$, together with the carbon atom to which they are attached, can also form a cycloalkyl ring containing 3 to 8 carbon atoms, preferably a spirocyclopropyl, spirocyclobutyl, spirocyclopentyl, spirocyclohexyl or spirocycloheptyl radical. Furthermore, $R_1$ and $R_2$ together can form an alkylidene radical containing up to 6 carbon atoms or a cycloalkylidene radical containing 3 to 8 carbon atoms, preferably methylidene, ethylidene, isopropylidene, cyclopentylidene or cyclohexylidene radicals.

If $R_3$ signifies a radical of the general formula:

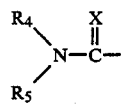

which can be in the 5-, 6-, 7- or 8-position of the isoquinoline-1,3-dione, then the 6- and 7-positions are especially preferred. The substituents $R_4$ and $R_5$ can be hydrogen atoms, straight-chained or branched alkyl radicals containing up to 8 and preferably up to 5 carbon atoms, trihaloalkyl radicals containing up to 3 carbon atoms, preferably a trifluoromethyl radical, cycloalkyl or cycloalkenyl radicals containing 3 to 7 carbon atoms but preferably with 5 or 6 carbon atoms, dialkylaminoalkyl, alkoxycarbonylalkyl or alkylcarbonyl radicals, in which the alkyl and/or alkoxy moieties contain up to 5 and preferably up to 3 carbon atoms, or aryl or hetaryl radicals. X is preferably an oxygen or sulphur atom or a radical of the general formula $=N-R_6$, in which $R_6$ is a hydrogen atom, an alkyl radical containing up to 3 carbon atoms, preferably a methyl, ethyl or isopropyl radical, or a cyano group. Aryl radicals can be, for example, optionally substituted phenyl or naphthyl radicals and hetaryl radicals can be, for example, optionally substituted pyridyl or pyrrolyl radicals.

The compounds of general formula (I) can be prepared, for example, either (a) by reacting an aminoisoquinoline-1,3-dione of the general formula:

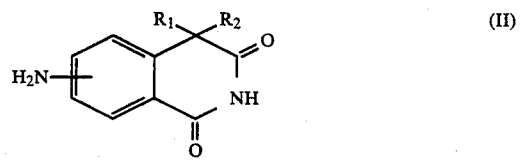

in which $R_1$ and $R_2$ have the above-given meanings, with a compound of the general formula:

or

in which $R_4$, $R_5$ and X have the above-given meanings, or with a compound of the general formula:

in which $R_4$, $R_5$ and X have the above-given meanings and Z is a group which can be split off, to give a compound of general formula (I); or (b) by reacting a compound of the general formula:

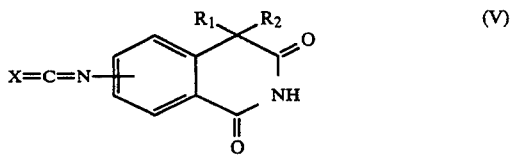

in which $R_1$, $R_2$ and X have the above-given meanings, or a compound of the general formula:

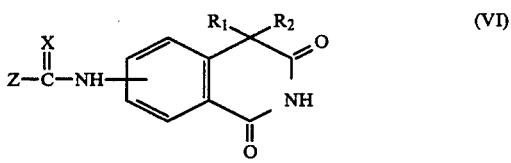

in which $R_1$, $R_2$, X and Z have the above-given meanings, with an amine of the general formula:

$$R_4-NH-R_5 \quad (VIII)$$

in which $R_4$ and $R_5$ have the above-given meanings, to give a compound of general formula (I).

A group Z which can be split off in compounds of the general formula (IV) or (VI) is usually a halogen atom, for example a chlorine, bromine or iodine atom, or also some other radical which can be split off, for example a mesylate, tosylate, phenoxy, methylthio or phenylthio radical.

Reactions of compounds of general formula (II) with compounds of general formula (III) or of compounds of general formula (V) with compounds of general formula (VII) are advantageously carried out in aprotic solvents, for example methylene chloride, chloroform, diethyl ether, tetrahydrofuran, dioxan, toluene or dimethylformamide, at a temperature of from $-70°$ C. to $200°$ C. but preferably of from $0°$ to $100°$ C.

Reactions of compounds of general formula (II) with compounds of general formula (IV) or of compounds of general formula (VI) with compounds of general formula (VII) can, depending upon the nature of the group Z which can be split off, be carried out not only in protic but also in aprotic solvents, such as water, alcohols, methylene chloride, chloroform, diethyl ether, tetrahydrofuran, dioxan, toluene or dimethylformamide, at a temperature of from $-70°$ to $200°$ C. but preferably of from $0°$ to $100°$ C.

Furthermore, compounds of general formula (I) can also be subsequently converted into other compounds of general formula (I). This applies, for example, to: (a) the conversion of compounds of general formula (I), in which $R_1$, $R_2$ and $R_3$ have the above-given meanings and X is an oxygen atom, into other compounds of general formula (I), in which X is a sulphur atom, by reacting compounds of general formula (I) with a sulphur-transferring reagent, for example, phosphorus pentasulphide or 2,4-bis-(4-methoxyphenyl)-2,4-dithioxo-1,3,2,4-dithiadiphosphetane, in an appropriate solvent, for example tetrahydrofuran, dioxan, ethylene glycol dimethyl ether, benzene, toluene or pyridine, at a temperature of from $0°$ C. and the boiling temperature of the reaction mixture;

(b) the reaction of compounds of general formula (I), in which $R_3$ and X have the above-given meanings and $R_1$ and $R_2$ are hydrogen atoms, with compounds of the general formula:

$$R_7-CO-R_8 \quad (VIII)$$

in which $R_7$ and $R_8$, which can be the same or different, are alkyl radicals or together form a $C_4-C_7$-cycloalkylene radical which is optionally interrupted by a heteroatom or by a heteroatom substituted with an alkyl radical, in the presence of a base to give compounds of the general formula:

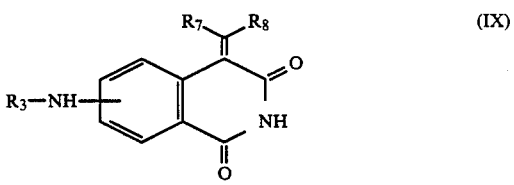

in which $R_7$ and $R_8$ have the above-given meanings, and subsequently the compounds of general formula (IX) are converted by catalytic hydrogenation into compounds of the general formula (I) in which $R_1$ and $R_2$ are hydrogen atoms.

The condensation of isoquinoline-1,3-dione with a compound of general formula (VIII) takes place in the presence of a base, preferably of sodium or potassium hydroxide.

The catalytic hydrogenation of compounds of general formula (IX) preferably takes place with palladium/charcoal in an alcoholic medium.

Furthermore, the compounds obtained of general formula (I) can subsequently, if desired, be converted into their physiologically acceptable acid-addition salts with inorganic or organic acids. As acids for this purpose, there can be used, for example, hydrochloric acid, hydrobromic acid, sulphuric acid, phosphoric acid, fumaric acid, succinic acid, tartaric acid, citric acid, lactic acid, maleic acid or methanesulphonic acid.

As already mentioned hereinbefore, the new compounds of general formula (I), the tautomers thereof and the physiologically acceptable acid-addition salts thereof display superior pharmacological properties with a long period of action, especially a blood pressure lowering and/or positive inotropic action and/or influence the thrombocyte function and improve the microcirculation.

For the preparation of pharmaceutical compositions, the compounds of general formula (I) are mixed in known manner with appropriate pharmaceutical carrier substances, aroma, flavouring and colouring materials and formed, for example, in tablets or dragees or, with the addition of appropriate adjuvants, are suspended or dissolved in water or an oil, for example olive oil.

The new compounds of general formula (I) according to the present invention and the salts thereof can be administered enterally or parenterally in liquid or solid form. As injection medium, it is preferred to use water which contains the additives usual in the case of injection solutions, such as stabilising agents, solubilising agents or buffers.

Additives of this type include, for example, tartrate and citrate buffers, ethanol, complex forming agents (such as ethylenediamine-tetraacetic acid and the non-toxic salts thereof) and high molecular weight polymers (such as liquid polyethylene oxide) for viscosity regulation. Solid carrier materials include, for example, starch, lactose, mannitol, methyl cellulose, talc, highly dispersed silicic acids, high molecular weight fatty acids (such as stearic acid), gelatine, agar-agar, calcium phosphate, magnesium stearate, animal and vegetable fats and solid high molecular weight polymers (such as polyethylene glycols). Compositions which are suitable for oral administration can, if desired, contain flavouring and sweetening agents.

The compounds according to the present invention are usually administered in amounts of from 10 to 500 mg. per day, referred to a body weight of 75 kg. It is preferred to administer 1 to 2 tablets 2 or 3 times a day with a content of active material of from 5 to 200 mg. The tablets can also be retarded, in which case 1 to 2 tablets with 10 to 500 mg. of active material have to be given once per day. The active material can also be administered by injection 1 to 8 times per day or by continuous infusion, in which case amounts of from 5 to 200 mg./day normally suffice.

Preferred compounds according to the present invention, apart from those mentioned in the Examples, are the following and the tautomers thereof:

N-(4,4-dimethyl-1,2,3,4-tetrahydro-1,3-dioxo-5-isoquinolinyl)-urea
N-methyl-N'-(4,4-dimethyl-1,2,3,4-tetrahydro-1,3-dioxo-5-isoquinolinyl)-urea
N-propyl-N'-(4,4-dimethyl-1,2,3,4-tetrahydro-1,3-dioxo-5-isoquinolinyl)-urea
N-(4,4-dimethyl-1,2,3,4-tetrahydro-1,3-dioxo-6-isoquinolinyl)-urea
N-ethyl-N'-(4,4-dimethyl-1,2,3,4-tetrahydro-1,3-dioxo-6-isoquinolinyl)-urea
N-propyl-N'-(4,4-dimethyl-1,2,3,4-tetrahydro-1,3-dioxo-6-isoquinolinyl)-urea
N-methyl-N'-(4,4-diethyl-1,2,3,4-tetrahydro-1,3-dioxo-6-isoquinolinyl)-urea
N-(1,2,3,4-tetrahydro-1,3-dioxo-7-isoquinolinyl)-urea
N-methyl-N'-(4-methyl-1,2,3,4-tetrahydro-1,3-dioxo-7-isoquinolinyl)-urea
N-methyl-N'-(4-allyl-1,2,3,4-tetrahydro-1,3-dioxo-7-isoquinolinyl)-thiourea
N-ethyl-N'-(4-cyclopentyl-1,2,3,4-tetrahydro-1,3-dioxo-7-isoquinolinyl)-urea
N-isopropyl-N'-[4-(1-methyl-4-piperidinyl)-1,2,3,4-tetrahydro-1,3-dioxo-7-isoquinolinyl]-urea
N,N-dimethyl-N'-(4,4-diethyl-1,2,3,4-tetrahydro-1,3-dioxo-7-isoquinolinyl)-urea
N-phenyl-N'-[spiro(cyclopentan-1,4'-1',2',3',4'-tetrahydro-1',3'-dioxo-7'-isoquinolinyl)]-urea
N-(4-pyridyl)-N'-(4,4-diethyl-1,2,3,4-tetrahydro-1,3-dioxo-7-isoquinolinyl)-urea
N-acetyl-N'-[spiro(cyclopentan-1,4'-1',2',3',4'-tetrahydro-1',3'-dioxo-7'-isoquinolinyl)]-urea
N-cyclohexyl-N'-(4,4-dimethyl-1,2,3,4-tetrahydro-1,3-dioxo-7-isoquinolinyl)-urea
N-(2-cyclopenten-1-yl)-N'-(4,4-dimethyl-1,2,3,4-tetrahydro-1,3-dioxo-7-isoquinolinyl)-urea
N-methyl-N'-(4,4-dimethyl-1,2,3,4-tetrahydro-1,3-dioxo-7-isoquinolinyl)-guanidine
N-cyano-N'-(4,4-dimethyl-1,2,3,4-tetrahydro-1,3-dioxo-7-isoquinolinyl)-guanidine
N-methyl-N'-cyano-N''-(4,4-dimethyl-1,2,3,4-tetrahydro-1,3-dioxo-7-isoquinolinyl)-guanidine
N-methyl-N'-(4,4-dimethyl-1,2,3,4-tetrahydro-1,3-dioxo-8-isoquinolinyl)-urea
N-ethyl-N'-(4,4-dimethyl-1,2,3,4-tetrahydro-1,3-dioxo-8-isoquinolinyl)-urea
N-propyl-N'-(4,4-dimethyl-1,2,3,4-tetrahydro-1,3-dioxo-8-isoquinolinyl)-urea.

The following Examples are given for the purpose of illustrating the present invention:

EXAMPLE 1

N-(4,4-Dimethyl-1,2,3,4-tetrahydro-1,3-dioxo-7-isoquinolinyl)-urea 1.3 g. (6.3 mMole) 7-amino-4,4-dimethylisoquinoline-1,3-dione was suspended in 30 ml. 2N acetic acid, mixed with 1.0 g. (12.5 mMole) potassium isocyanate and stirred for 6 hours at 80° C. The reaction mixture was cooled and the precipitate was filtered off with suction and washed with water. The residue was dissolved in dilute aqueous sodium hydroxide solution, the solution was neutralised with dilute hydrochloric acid, the residue was filtered off with suction and, for purification, worked up with ethanol and filtered off with suction. Yield: 0.6 g. (38.5% of theory); m.p. 260°–264° C.

EXAMPLE 2

N-Methyl-N'-(4,4-dimethyl-1,2,3,4-tetrahydro-1,3-dioxo-7-isoquinolinyl)-urea 3 g. (14.7 mMole) 7-amino-4,4-dimethylisoquinoline-1,3-dione were dissolved in 100 ml. methylene chloride, mixed with 5 ml. methyl isocyanate, while cooling, and then further stirred for 2 hours at 25° C. Subsequently, the reaction mixture was evaporated, cooled, filtered off with suction and recrystallised from methanol. Yield: 3.7 g. (96.4% of theory); m.p. 257°–258° C.

The following compounds were obtained analogously to Example 2:

| | designation | yield (%) | m.p. (°C.) (solvent) |
|---|---|---|---|
| (a) | N—ethyl-N'—(4,4-dimethyl-1,2,3,4-tetrahydro-1,3-dioxo-7-isoquinolinyl)-urea from 7-amino-4,4-dimethylisoquinoline-1,3-dione and ethyl isocyanate | 75 | 225–228 ethanol |
| (b) | N—isopropyl-N'—(4,4-dimethyl-1,2,3,4-tetrahydro-1,3-dioxo-7-isoquinolinyl)-urea from 7-amino-4,4-dimethylisoquinoline-1,3-dione and isopropyl isocyanate | 60.5 | 190–192 ethyl acetate |
| (c) | N—phenyl-N'—(4,4 dimethyl-1,2,3,4-tetrahydro-1,3-dioxo-7-isoquinolinyl)-urea from 7-amino-4,4-dimethylisoquinoline-1,3-dione and phenyl isocyanate | 83 | >300 ethanol |
| (d) | N—acetyl-N'—(4,4-dimethyl-1,2,3,4-tetrahydro-1,3-dioxo-7-isoquinolinyl)-urea from 7-amino-4,4-dimethyl-isoquinoline-1,3-dione and acetyl isocyanate | 82.5 | 284–287 methanol |
| (e) | N—(2-ethoxycarbonyl)-ethyl-N'—(4,4-dimethyl-1,2,3,4-tetrahydro-1,3-dioxo-7-isoquinolinyl)-urea from 7-amino-4,4-dimethyl-iso- | 63.5 | 192–193 ethanol |

| | designation | yield (%) | m.p. (°C.) (solvent) |
|---|---|---|---|
| | quinoline-1,3-dione and (2-ethoxycarbonyl)-ethyl isocyanate | | |
| (f) | N—methyl-N'—[spiro(cyclopentan-1,4'-1',2',3',4'-tetrahydro-1',3'-dioxo-6'-isoquinolinyl)]-urea from 7'-amino-spiro(cyclopentan-1,4'-2H',4H'—isoquinolin)-1',3'-dione and methyl isocyanate | 91 | >300 ethanol |

EXAMPLE 3

N-Methyl-N'-(4,4-dimethyl-1,2,3,4-tetrahydro-1,3-dioxo-7-isoquinolinyl)-thiourea 1.3 g. (6.3 mmol) 7-Amino-4,4-dimethyl-isoquinolin-1,3-dione were dissolved in 30 ml. chloroform, mixed with 1.4 g. methyl isothiocyanate and boiled under reflux for 6 hours. The reaction mixture was then cooled and the precipitate was filtered off with suction and recrystallised from ethanol. Yield: 0.8 g. (46% of theory); m.p. 206°–207° C.

EXAMPLE 4

N,N-Dimethyl-N'-(4,4-dimethyl-1,2,3,4-tetrahydro-1,3-dioxo-7-isoquinolinyl)-urea 1.3 g. (6.3 mMole) 7-amino-4,4-dimethylisoquinoline-1,3-dione was dissolved in 30 ml. pyridine, mixed, while cooling with ice, with 1.5 g. dimethylcarbamoyl chloride and the reaction mixture further stirred for 4 hours at 25° C. Subsequently, the reaction mixture was distilled to dryness, the residue was taken up in methylene chloride, washed with water, dried and the methylene chloride distilled off. The residue was recrystallised from ethanol. Yield 1.1 g. (63.6% of theory); m.p. 256°–258° C.

EXAMPLE 5

N-(4-Pyridyl)-N'-(4,4-dimethyl-1,2,3,4-tetrahydro-1,3-dioxo-7-isoquinolinyl)-urea monohydrochloride 1.5 g. (7.34 mMole) 7-amino-4,4-dimethylisoquinoline-1,3-dione was dissolved in 40 ml. dioxan, 3.6 g. 4-pyridinecarboxylic acid azide were added thereto and the reaction mixture further stirred for 4 hours at 80° C. Subsequently, the solvent was distilled off, the residue was suspended in ethanol, mixed with ethanolic hydrochloric acid and the residue filtered off with suction. The residue was dissolved in 2N aqueous sodium hydroxide solution, the sodium salt which precipitated out after a short time was filtered off with suction and, after again suspending in water, was acidified with 2N hydrochloric acid and filtered off with suction. Yield 1.6 g. (60.4% of theory); m.p. 255°–259° C., as hydrochloride.

EXAMPLE 6

N-Cyano-N'-(4,4-dimethyl-1,2,3,4-tetrahydro-1,3-dioxo-7-isoquinolinyl)-urea 2 g. (5.7 mMole) N-cyano-N'-(4,4-dimethyl-1,2,3,4-tetrahydro-1,3-dioxo-7-isoquinolinyl)-O-phenylisourea were suspended in 100 ml. ethanol and gaseous ammonia passed in at 80° C. After 2 hours, the reaction mixture was cooled, filtered off with suction and the residue again recrystallised from ethanol. Yield 1.3 g. (83.8% of theory); m.p. 280°–282° C.

The starting material was prepared as follows:

5.5 g. (23 mMole) N-cyanodiphenoxyimidocarbonate and 4.7 g. (23 mMole) 7-amino-4,4-dimethylisoquinoline-1,3-dione were stirred in 110 ml. isopropanol for 16 hours at 50° C. Subsequently, the reaction mixture was cooled, filtered off with suction and washed with isopropanol. The residue was recrystallised from ethanol. There were obtained 4.1 g. (51% of theory) N-cyano-N'-(4,4-dimethyl-1,2,3,4-tetrahydro-1,3-dioxo-7-isoquinolinyl)-O-phenylisourea; m.p. 214°–216° C.

The following compound was obtained analogously to Example 6:

| | designation | Yield (%) | m.p. (°C.) (solvent) |
|---|---|---|---|
| (a) | N—cyano-N'—methyl-N''-(4,4-dimethyl-1,2,3,4-tetrahydro-1,3-dioxo-7-isoquinolinyl)-guanidine from N—cyano-N'—(4,4-dimethyl-1,2,3,4-tetrahydro-1,3-dioxo-7-isoquinolinyl)-O—phenylisourea and 35% methylamine solution | 82.7 | 258–260 methanol |

EXAMPLE 7

N-(2-Dimethylamino)-ethyl-N'-(4,4-dimethyl-1,2,3,4-tetrahydro-1,3-dioxo-7-isoquinolinyl)-urea 3.6 g. (11.6 mMole) N-(2-chloroethyl)-N'-(4,4-dimethyl-1,2,3,4-tetrahydro-1,3-dioxo-7-isoquinolinyl)urea were mixed with 30 ml. 40% dimethylamine solution and stirred for 8 hours at 30° C. Subsequently, the solvent was distilled off and the residue was worked up with 2N hydrochloric acid and filtered off with suction. The aqueous acidic phase was neutralised, extracted with methylene chloride, dried, evaporated and the residue obtained recrystallised from ethanol. Yield 1.9 g. (51.5% of theory); m.p. 204°–205° C.

The N-(2-chloroethyl)-N'-(4,4-dimethyl-1,2,3,4-tetrahydro-1,3-dioxo-7-isoquinolinyl)-urea used as starting material was prepared analogously to Example 2 from 7-amino-4,4-dimethylisoquinoline-1,3-dione and 2-chloroethyl isocyanate. Yield 90% of theory; m.p. 177°–179° C., after crystallisation from ethanol.

EXAMPLE 8

Pharmaceutical Activity

Examination method:

Male Sprague-Dawley rats weighing between 350 and 450 g were narcotized by intraperitoneal injection of a barbiturate and fitted with instrumentation for the examinations as follows:

A pressure measuring catheter (Millar Mikrotip/diameter 0.5 mm) was inserted through the arteria carotis dextra into the left ventricle. The pressure inside the left ventricle was continually registered through this catheter. The signal from this Mikrotip was electronically differentiated and $(dp/dt)_{60}$—the slope of the pressure-time curve at a pressure of 60 mmHg—was taken as a measure for the inotropy.

A polypropylene catheter was inserted through an arteria femoralis into the abdominal aorta for the direct measurement of the arterial blood pressure.

The EEG was traced with subcutaneous insertion electrodes.

During the preparation of the animal and during the entire test period the rats were fixed on an electrically heated and thermostated operating table.

Procedure

The test substances were always introduced by intravenous injection, with an injection volume, per injection, of 1 ml/kg body weight. In intervals of 10 min each, doses increasing from 0.01 to 30 mg of the test substances were intravenously injected. In this way dose effect curves for the measured parameters for the investigated substances were obtained.

From the measured data, using a regression calculation, equipotent doses for the positively inotropic effect $(dp/dt)_{60}$ were calculated. In addition, as criterion for the effectiveness of the substances, the maximum effect obtained maximal increase of $(dp/dt)_{60}$ and its corresponding dose were determined. The table that follows shows the equipotent doses ($DE_{1,5}$=the dose in mg/kg that leads to an increase of $(dp/dt)_{60}$ of 1.5 mHg/sec and the maximal effectiveness ($W_{max}$=the maximal increase of $(dp/dt)_{60}$. Besides, the corresponding injected dose is shown.

| Substance | $DE_{1,5}$ mHg/sec [mg/kg i. v.] | $W_{max}$ [mHg/sec] | $W_{max}$ [mg/kg i. v.] |
|---|---|---|---|
| Ref. 1 | 1.17 | 3.5 | 10 |
| Ref. 2 | >>3.0 | 0.6 | 3.0 |
| 1 | — | 0.3 | 3.0 |
| 2 | 0.28 | 3.8 | 10.0 |
| 2a | >1.0 | 2.7 | 10.0 |
| 2b | >3.0 | 2.0 | 10.0 |
| 2d | >3.0 | 2.3 | 10.0 |
| 3 | — | 0.6 | 1.0 |
| 4 | — | 1.0 | 3.0 |
| 5 | — | 0.3 | 1.0 |
| 6 | 0.47 | 2.0 | 1.0 |
| 6a | — | 0.1 | 0.03 |
| 7 | — | 1.5 | 3.0 |

The values show, that the substances of Ex. 2 and 6 are more potent than the substance, used as standards (Ref. 1 and Ref. 2).

Ref. 1: 3-Amino-6-methyl-5-phenyl-2(1H)-pyrridinone-methanesulfonate (from British patent application GB 2,070,606)

Ref 2: 3,4-Dihydro-6-[4-(3,4-dimethoxybenzoyl)-1-piperazinyl]-2(1H)-quinolinone (from U.S. patent application U.S. Pat. No. 4,415,572)

It will be understood that the specification and examples are illustrative but not limitative of the present invention and that other embodiments within the spirit and scope of the invention will suggest themselves to those skilled in the art.

What is claimed is:

1. An isoquinoline-1,3-dione compound of the formula

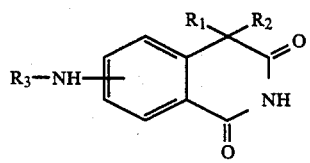
(I)

wherein $R_1$ is hydrogen, a $C_1$-$C_6$ alkyl, a $C_2$-$C_6$ alkenyl or $C_3$-$C_7$ cycloalkyl wherein said cycloalkyl is optionally interrupted by a heteroatom or by a heteroatom substituted with a $C_1$-$C_6$ alkyl radical wherein said heteroatomic heterocycloalkyl is piperidyl or N-alkyl piperidyl;

$R_2$ is hydrogen a $C_1$-$C_6$ alkyl or a $C_2$-$C_6$ alkenyl radical or, $R_2$ together with $R_1$, is a $C_3$-$C_8$ cycloalkyl ring, $C_3$-$C_8$ heterocycloalkylene, up to 6 carbon alkylidene or $C_3$-$C_8$ cycloalkylidene wherein said radical is optionally interrupted by a heteroatom or by a heteroatom substituted by a $C_1$-$C_6$ alkyl radical wherein said heteroatomic cycloalkyl is piperidyl or N-alkyl piperidyl; and $R_3$ is

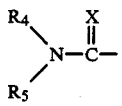

which can be in the 5-, 6-, 7- or 8-position of the isoquinoline-1,3-dione and in which $R_4$ and $R_5$, which can be the same or different, are hydrogen, $C_1$-$C_8$ alkyl, $C_1$-$C_8$ alkyl, $C_1$-$C_3$ trihaloalkyl, $C_3$-$C_7$ cycloalkyl, $C_3$-$C_7$ cycloalkyl, $C_3$-$C_7$ cycloalkenyl, pyridyl, pyrrolyl, phenyl, naphthyl or dialkylaminoalkyl, alkoxycarbonylalkyl, alkylcarbonyl wherein the alkyl or alkoxy moieties of said dialkylaminoalkyl, alkoxycarbonylalkyl and alkylcarbonyl groups have 1-5 carbons, and X is an oxygen or sulphur atom or a radical of the formula =N—$R_6$, in which $R_6$ is a hydrogen atom, a cyano group or $C_1$-$C_6$ alkyl; and the physiologically acceptable salts thereof.

2. A compound of claim 1, wherein $R_1$ and $R_2$ are the same or different and are hydrogen, methyl, ethyl, allyl or, $R_1$ and $R_2$, together with the carbon atom to which they are attached, represent a spirocyclopentyl or spirocyclohexyl and $R_3$ represents a radical of the formula:

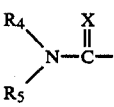

which can be in the 6- or 7-position of the isoquinoline-1,3-dione and wherein $R_4$ and $R_5$, whih can be the same or different, are hydrogen, methyl, ethyl, isopropyl, phenyl, pyridyl, acetyl, ethoxycarbonylethyl or dimethylaminoethyl, X is oxygen or sulphur or a radical of the general formula =N—$R_6$ in which $R_6$ is a cyano group; and the physiologically acceptable salts thereof.

3. A compound of claim 1 or 2, wherein $R_1$ and $R_2$ are methyl or, together with the carbon atom to which they are attached, form a spirocyclopentyl radical and $R_3$ is a radical of the formula:

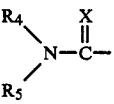

which is in the 7-position of the isoquinoline-1,3-dione and in which $R_4$ and $R_5$, which are the same or different, are hydrogen or methyl and X is an oxygen atom or a cyanimino group; and the physiologically acceptable salts thereof.

4. A compound of claim 1 or 2 wherein
$R_2$ is H and,
$R_1$ is a branched 3–7 carbon alkyl or cycloalkyl optionally interrupted by a heteroatom or by a heteroatom substituted by an alkyl wherein said heterocycloalkyl is piperidyl or N-alkyl piperidyl.

5. A compound of claim 4 wherein $R_1$ is selected from the group consisting of isopropyl, 3-pentyl, cyclopentyl, cyclohexyl, piperidyl and N-methylpiperidyl.

6. A compound of claim 1 or 2 wherein $R_1$ is the same as $R_2$ and represents a $C_1$–$C_6$ alkyl.

7. A compound of claim 1 or 2 wherein $R_1$ and $R_2$ together with the carbon atom to which they are attached comprise a $C_3$–$C_8$ cycloalkyl ring selected from the group consisting iof spirocyclopropyl, spirocyclobutyl, spirocyclopentyl, spirocyclohexyl and spirocycloheptyl.

8. A compound of claim 1 or 2 wherein $R_1$ and $R_2$ together comprise an alkylidene or cycloalkylidene selected from the group consisting of methylidene, ethylidene, isopropylidene, cyclopentylidene and cyclohexylidene.

9. A compound of claims 1 or 2 wherein $R_4$ and $R_5$ comprise hydrogen $C_1$–$C_5$ alkyl, a trifluoromethyl,
and further comprise dialkylaminoalkyl, alkoxycarbonylalkyl and alkylcarbonyl wherein alkyl or alkoxyl comprise up to three carbon atoms.

10. A compound of claim 1 or 2 wherein $R_6$ is hydrogen, methyl, ethyl, isopropyl or cyano.

11. isoquinoline-1,3-dione compound as in claim 1 designated N-methyl-N'-(4,4-dimethyl-1,2,3,4-tetrahydro-1,3-dioxo-7-isoquinolinyl)-urea, and physiologically active salts thereof.

12. Isoquinoline-1,3-dione compound as in claim 1 designated N-ethyl-N'-(4,4-dimethyl-1,2,3,4-tetrahydro-1,3-dioxo-7-isoquinolinyl)-urea, and physiologically active salts thereof.

13. Isoquinoline-1,3-dione compound as in claim 1 designated N-cyano-N'-(4,4-dimethyl-1,2,3,4-tetrahydro-1,3-dioxo-7-isoquinolinyl)-urea, and physiologically active salts thereof.

14. Isoquinoline-1,3-dione compound as in claim 1 designated N-cyano-N'-methyl-N''-(4,4-dimethyl-1,2,3,4-tetrahydro-1,3-dioxo-7-isoquinolinyl)-guanidine, and physiologically active salts thereof.

15. A pharmaceutical composition, containing an effective amount of at least one compound of claim 1 or 2 for the prophylaxis or treatment of heart and circulatory disease in a pharmaceutically acceptable carrier.

16. A pharmaceuticalcomposition, containing an effective amount of at least one compound of claim 3 for the prophylaxis or treatment of heart and circulatory disease in a pharmaceutically acceptable carrier.

17. A pharmaceutical composition, for the prophylaxis or treatment of heart and circulatory disease in a pharmaceutically acceptable carrier, containing an effective amount of at least one compound designated
N-methyl-N'-(4,4-dimethyl-1,2,3,4-tetrahydro-1,3-dioxo-7-isoquinolinyl)-urea,
N-ethyl-N'-(4,4-dimethyl-1,2,3,4-tetrahydro-1,3-dioxo-7-isoquinolinyl)-urea,
N-cyano-N'-(4,4-dimethyl-1,2,3,4-tetrahydro-1,3-dioxo-7-isoquinolinyl)-urea,
N-cyano-N'-methyl-N''-(4,4-dimethyl-1,2,3,4-tetrahydro-1,3-dioxo-7-isoquinolinyl)-guanidine.

18. A method for the treatment or prophylaxis of heart and circulatory disease comprising administering a pharmaceutically effective amount of the compound of claim 1 or 2.

19. A method for the treatment or prophylaxis of heart and circulatory disease comprising administering a pharmaceutically effective amount of the compound of claim 3.

20. A method for the treatment or prophylaxis of heart and circulatory disease comprising administering a pharmaceutically effective amount of at least one of the compound designated
N-methyl-N'-(4,4-dimethyl-1,2,3,4-tetrahydro-1,3-dioxo-7-isoquinolinyl)-urea,
N-ethyl-N'-(4,4-dimethyl-1,2,3,4-tetrahydro-1,3-dioxo-7-isoquinolinyl)-urea,
N-cyano-N'-(4,4-dimethyl-1,2,3,4-tetrahydro-1,3-dioxo-7-isoquinolinyl)-urea, and
N-cyano-N'-methyl-N''-(4,4-dimethyl-1,2,3,4-tetrahydro-1,3-dioxo-7-isoquinolinyl)-guanidine.

21. The method of claim 18 wherein 10 to 500 mg per 75 kg body weight are administered per day.

22. The method of claim 19 wherein 10 to 500 mg per 75 kg body weight are administered per day.

23. The method of claim 20 wherein 10 to 500 mg per 75 kg body weight are administered per day.

* * * * *

UNITED STATES PATENT AND TRADEMARK OFFICE
CERTIFICATE OF CORRECTION

PATENT NO.   :   4,824,835

DATED        :   April 25, 1989

INVENTOR(S)  :   Alfred Mertens, et al.

It is certified that error appears in the above-identified patent and that said Letters Patent is hereby corrected as shown below:

```
Abstract, line 16
  of text       :    delete "dealkylaminoalkyl" and insert
                     -- dialkylaminoalkyl --.

Col. 10, line 52 :   delete "whih" and insert -- which --.

Col. 11, line 36
  new claim 11  :    delete "isoquinoline" and insert
                     -- Isoquinoline --.

Col. 12, line 7
  new claim 16  :    insert a space --  -- between
                     pharmaceutical and composition.
```

Signed and Sealed this

Fifth Day of June, 1990

Attest:

HARRY F. MANBECK, JR.

*Attesting Officer*      *Commissioner of Patents and Trademarks*